United States Patent [19]

Chalifoux

[11] Patent Number: 5,197,881
[45] Date of Patent: Mar. 30, 1993

[54] DENTAL IMPLANT SYSTEM AND APPARATUS

[75] Inventor: Paul R. Chalifoux, Wellesley, Mass.

[73] Assignee: Wellesley Research Associates, Inc., Wellesley, Mass.

[21] Appl. No.: 814,507

[22] Filed: Dec. 30, 1991

[51] Int. Cl.⁵ ............................................. A61C 8/00
[52] U.S. Cl. .................................................... 433/173
[58] Field of Search ................. 433/173, 174, 175, 176

[56] References Cited

U.S. PATENT DOCUMENTS

| | | | |
|---|---|---|---|
| 2,857,670 | 10/1958 | Kiernan, Jr. | 433/175 |
| 3,497,953 | 3/1970 | Weissman | 433/173 |
| 3,579,831 | 5/1971 | Stevens | 433/174 |
| 3,618,212 | 11/1971 | Weissman | 433/173 |
| 4,624,673 | 11/1986 | Meyer | 433/173 |

FOREIGN PATENT DOCUMENTS 3300764  7/1984  Fed. Rep. of Germany ...... 433/173

Primary Examiner—John J. Wilson
Attorney, Agent, or Firm—Paul J. Cook

[57] ABSTRACT

A dental implant is provided for insertion into the jawbone of a patient for the purpose of building a dental prostheses thereon. The implant includes a central hole for accommodating a dental post having wings. The dental post wings fit into mating slots in the implant hole in order to effect retention of the post in the implant while avoiding rotation of the positioned post.

10 Claims, 5 Drawing Sheets

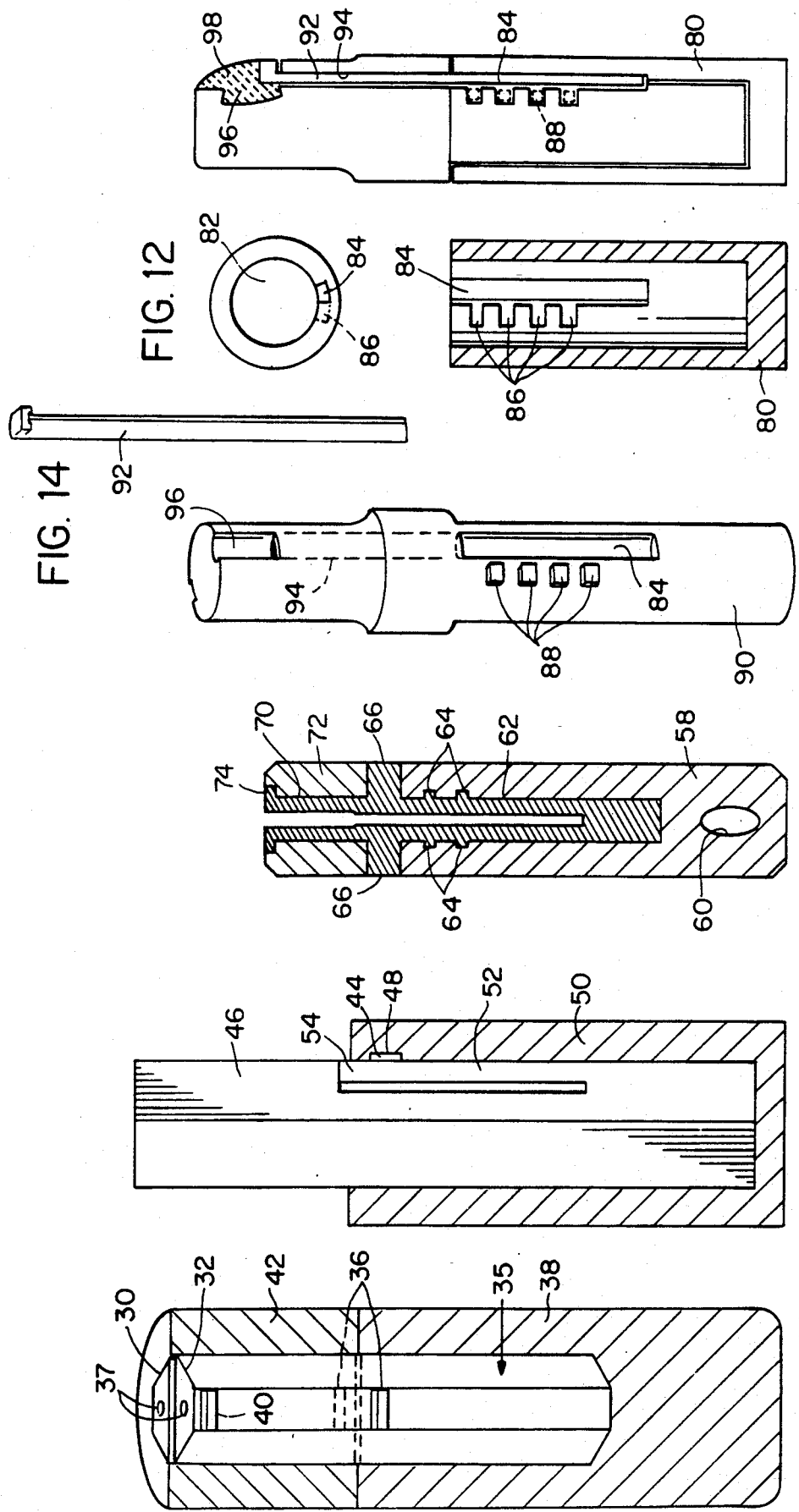

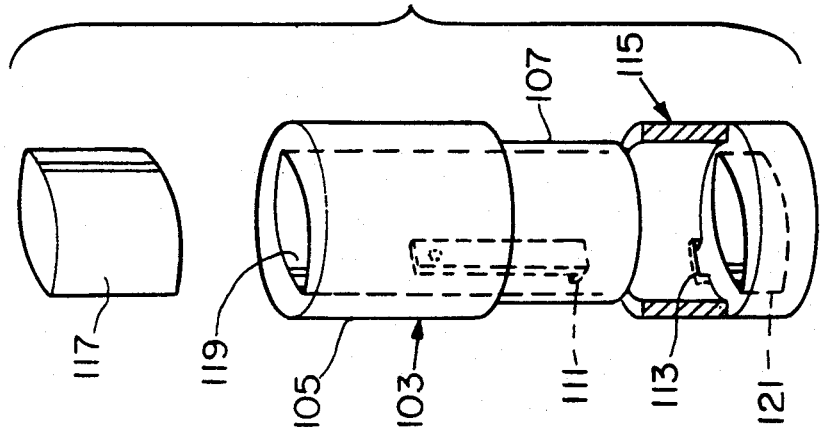
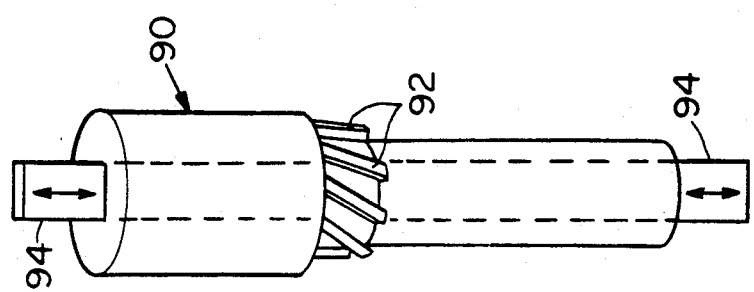
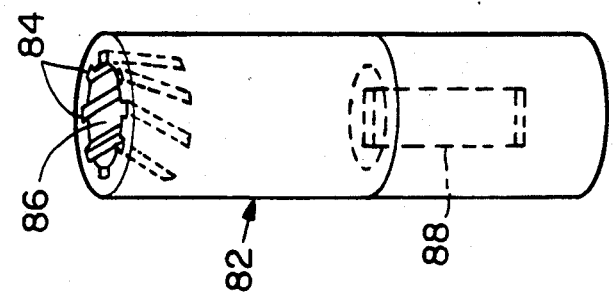
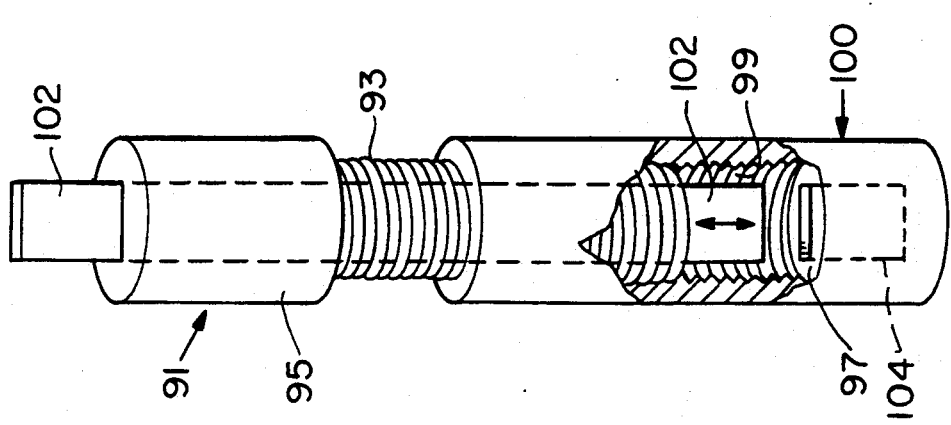
FIG. 25
FIG. 24
FIG. 23
FIG. 22

DENTAL IMPLANT SYSTEM AND APPARATUS

BACKGROUND OF THE INVENTION

This invention relates to a dental implant system which can be inserted into the jaw bone of a patient and can be utilized to improve retention of a dental restoration built onto the jaw bone.

Presently, dental implant systems are utilzied to fix a synthetic tooth structure to the jaw bone of a patient in order to replace a missing tooth. The implant system includes an implant which is inserted into a hole in the patient's jaw bone drilled by a dentist. The implant includes a hole designed to receive a dental post which, in turn, serves to retain a core upon which a tooth crown is built. After the implant is inserted into the jaw bone, it is covered by the patient's gum and allowed to heal from 3-6 months while the bone grows to surround and retain the implant. The gum then is opened to expose the implant. At this time, impressions are made or a post needed to support the crown is positioned into the implant. At the present time, these posts are screwed into place with the implant having a helical path and the post having a mating helical thread. The post bottom can have threads or can have a hollow core for a screw to unite the post and implant. A screw system alone does not provide an antirotation characteristic to the implant system and can unscrew and loosen unless multiple screws are employed. A problem with this system is that the screws break during implacement and during function. Also, the screws are small and may be dropped in the mouth accidently or they are difficult to place into the back portion of the mouth. After the post is positioned in the implant, it extends above the gum so that a dental prosthesis including a core can be retained in place. All posts must resist normal rotational forces which occur during normal or abnormal functions. In general, preformed posts do not provide good stability against rotational force because they are round and rotate easily when placed in a round hole in the implant. Screw type posts can exert large lateral stresses which lead to potential implant fixture fracture and tooth loss. If filling material is placed around a preformed post above the jawbone to accept a crown after the post is positioned, the strength and long term stability of this material becomes a weak link in long term success of the crown. In addition, proper design of the post above the jaw line is critical to resist rotation or dislodging of the filling material from the post.

It has been proposed in U.S. Pat. Nos. 4,480,997; 4,490,116 and Re 31,948, to utilize a threaded dental post which is introduced into the bore of a tooth stub by being rotated to thread the post into position. The dental post includes a stem portion having a slot extending through the stem thickness and along its length which renders the stem being formed of two legs each having its outside surface threaded. The outside surface of the legs intimately contact the walls of the bore so that the threads on the legs can engage the walls. In addition, a spring-like connection for the two legs is provided so that a radial outward spring force is applied to the legs to force them against the bore walls. These dental posts are undesirable since a rotational force must be applied to the post to position it properly into the bore. This positioning process is undesirable since it is time consuming and causes the patient discomfort. In addition, the possibility exists that the post will be threaded too far which will result in fracture. Furthermore, the radially outward forces of the legs on the tooth stub can result in fracture of the tooth stub over time. The same problems are present when these posts are used in conjunction with an implant positioned in a jawbone.

U.S. Pat. 1,534,409 discloses a two legged post having corrugated surfaces which fit into a root canal having generally parallel walls. This surface design materially reduces the post surface area which contacts the canal walls and thus post retention relies primarily upon cement adhesive strength.

Accordingly, it would be desirable to provide a dental implant having a bore for a dental post which can be inserted into a hole in the jaw. In addition, it would be desirable to provide a dental implant with means to provide mechanical interaction in order to retain the post in the implant hole while minimizing or eliminating forces on the implant walls exerted by the post. Furthermore, it would be desirable to provide a system for utilizing such a dental implant and post system which facilitates the placement of a core and a crown.

SUMMARY OF THE INVENTION

This invention provides a dental implant utilized in conjunction with a dental post in order to support dental prosthesis. The implant is sized to be positioned within a hole of the jaw bone of a patient. The implant has an internal hole or bore shaped so that after a dental post has been inserted into the bore of the implant, the dental post cannot be rotated. The wall of the implant bore is provided with one or more slots or indentations which are shaped to accept one or more extensions or wings which extend from the surface of the portion of the post which fits into the implant bore. Alternatively, the slot or indentation can be located on the bottom internal surface within which a key can fit. The key extends through the post and revents the post from rotating. The extension or wings of the dental post can be positioned within the implant slots either by being moved radially or rotationally into the slot(s). When a plurality of slots are utilized in the implant bore they can be positioned at different vertical positions and/or different radial positions at the same or different vertical height. A dental post having wings that are moved radially into the slots includes one or more flexible legs each having a wing. These legs can be compressed radially inward so that the post can be positioned within the implant bore and the leg then can be allowed to expand so that the wing(s) fit into the slot(s). Alternatively, the wings can be moved into the slot by means of a key which extends into a bore of the post to contact the wing and force it into a slot. Alternatively, when the wings are rotated into the slots, they can be positioned into holes on the top surface of the implant which interconnect with vertical paths in the implant. The vertical paths, in turn, connect with the slots. The wings are inserted into the vertical paths and then rotated into the slots.

BRIEF DESCRIPTION OF THE DRAWINGS

FIG. 8 is an isometric view of an implant-post-core system of this invention.

FIG. 9 is a side view of an alternative implant-post-core system of this invention.

FIG. 10 is a cross-sectional veiw of an alternative implant-post-core system of this invention.

FIG. 11 is an implant used with the post of FIG. 13.

FIG. 12 is a top view of the implant of FIG. 11.

FIG. 13 is an isometric view of a post of this invention.

FIG. 14 is a key used with the post of FIG. 13.

FIG. 15 shows the post of FIG. 13 and the implant of FIG. 11 in place.

FIG. 22 illustrates a post implant system of this invention wherein the post is held in place by a screw thread and a key.

FIG. 23 shows an implant having angled internal slots.

FIG. 24 shows a post and key which is used in conjunction with the implant of FIG. 23.

FIG. 25 shows an alternative post-implant system of this invention.

DESCRIPTION OF SPECIFIC EMBODIMENTS

Figure 7:
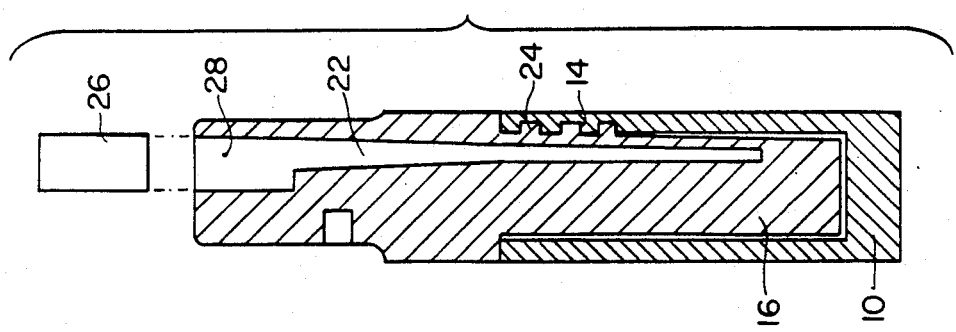
FIG. 7 is a side view of the post and implant of FIG. 5.
Figures 4, 5, 6:
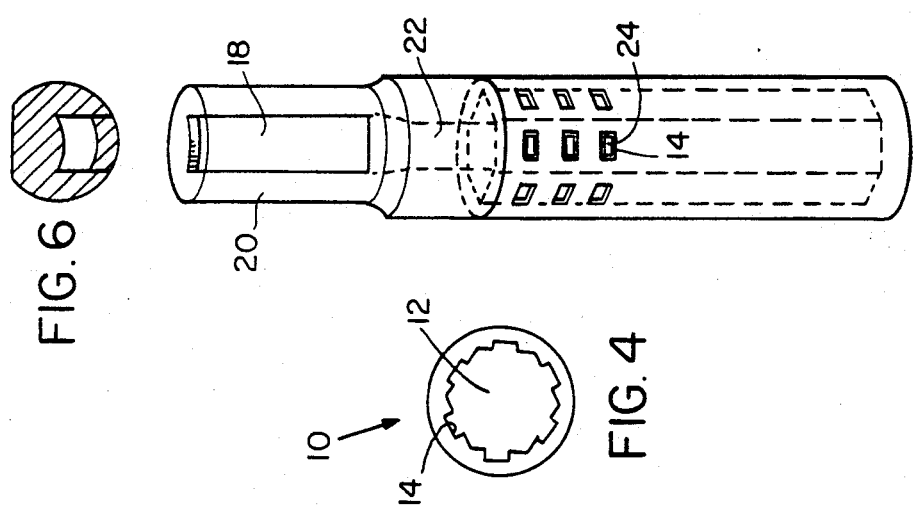
FIG. 4 is a cross-sectional view taken along line 4—4 of FIG. 3.
FIG. 5 shows the post of FIGS. 2 and 3 positioned into the implant of FIG. 1.
FIG. 6 is a top view of the post of FIG. 5.
Figure 3:
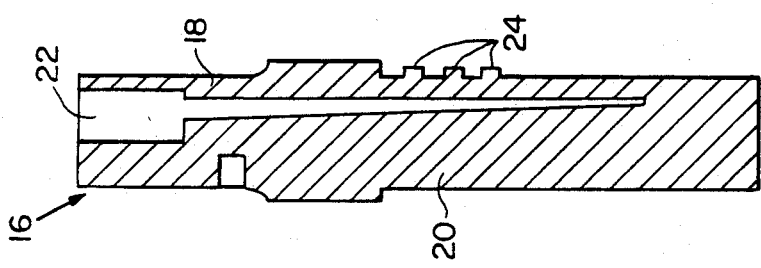
FIG. 3 is a side view of the post of FIG. 2.
Figure 2:
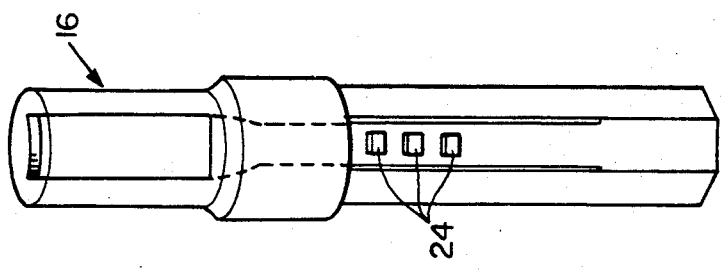
FIG. 2 is a front view of a post used with the implant of FIG. 1.
Figure 1:
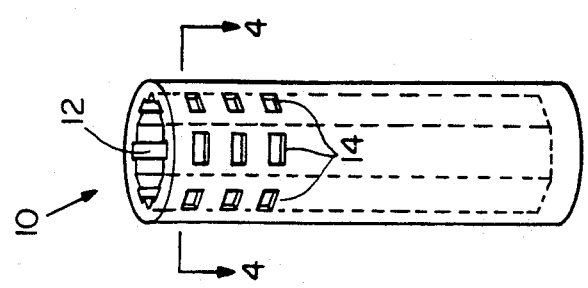
FIG. 1 is an isometric view of an implant of this invention.

The dental implant of this invention includes a bore having at least one slot which permits locking a mating dental post in the implant without the need for screwing the post in place. By eliminating the use of a threaded screw, pressure on the implant is eliminated. The slots utilized in the implant are discrete in that they are not in the shape of a continuous thread as would be necessary with a screw mechanism. The implant is utilized in conjunction with a dental post having a stem from which wings extend radially. The post and implant of this invention can be implanted under conditions to avoid the use of cement. Thus, the post can be removed, if desired, such as when an abcess occurs after implantation so that the abcess can be treated. The wings can be positioned by moving a portion of the post radially into position or by rotating the post into position or by employing a key structure to move a wing into position.

When a portion of the post is moved radially into position it is formed from a plurality of legs separated by a space. The legs can be radially compressed inward so that the wings can clear the top surface of the bore of the implant. When the compression force is released, the legs resume a position so that they are essentially parallel to each other and the wings fit into an indentation in the bore walls of the implant. The wings can be at the same or different heights. The wings can be the same or different sizes. The legs are not prestressed so as to avoid exertion of a force by the legs on the bore walls. By eliminating this stress in the legs, the implant fixture is not subjected to a continuing expansion force from within the implant. Therefore, the implant is less likely to fracture during normal use as compared to an implant containing a dental post that exerts a continuing expansion force on an implant.

In cases where the success of the implant is questionable, the post can be implanted without employing a dental cement in the post and implant. The wings mechanically lock the post in place, and, together with a key structure described below, lock the post and supported crown in place when the crown is cemented over the post. The elimination of cement within the implant and post is advantageous since, with present technology, when an implant fails and a post is present, the post cannot be removed for retreatment to eliminate infection. When the post is removable, as in the case when cement within post and implant is not utilized, surgery can be avoided and the implant can be treated to eliminate infection. A key apparatus can be provided which fits into the space between the post legs. The key prevents flexing of the legs after the crown and core have been positioned on the dental post.

In the embodiment wherein the dental post is rotated into position within the implant, flexible legs in the dental post need not be included. The stem portion of the dental post can be formed of a unitary construction wherein the wings are formed integrally with the post. The post is inserted into the implant bore so that the wings fit into vertical pathways formed within the bore walls of the implant which connect with the slots. When the wings have reached the same vertical position as the slots, the post is rotated so that the wings fit into the slots. A key can be inserted into the vertical pathways to prevent rotation of the post.

In still another embodiment, a movable wing in the post can be provided which wing is positioned by means of a spring or the like in the post. After the post is inserted into the implant, a key is inserted into a space within the post to exert force against the wing to position it within a slot of the implant. The key causes the wing to be maintained within the slot.

Referring to FIGS. 1 through 7, the dental implant 10 formed from any suitable dental material includes a hexagonal bore 12 and slots 14. The slots 14 are positioned at different vertical heights within the bore 12. The bore 12 can be of any desired shaped cross-section. The hexagonal shape permits positioning of a post in 6 different positions. Of course larger or smaller number of facets forming the bore shape can be used. The bore also can be circular, elliptical or the like. For convenience, the dental post 16 is shown with two legs 18 and 20. However, it is to be understood that up to eight legs can be formed conveniently with appropriate slots in stem section 22. The wings 24 are secured to and formed integrally with the legs 18 such as by conventional molding, machined or casting processes. The dental post 16 is inserted into the implant 10 by compressing flexible leg 18 radially inward so that the wings 24 clear the surface of the bore 12 and so that the post 16 can be inserted completely into bore 12. After the post 16 is inserted compression on the leg 18 is released and the wings 24 are positioned into slots 14. Thereafter, a key 26 is inserted into space 28 so that the wings 24 are maintained into the slots 14. Once, the post 16 is inserted into implant 10 rotation is prevented.

The dental post can be made of a variety of sizes. For example, a dental post can extend about 3 to 18 mm into the implant and 1 to 7 mm above the jaw bone. A typical dental post diameter can vary between about 1.5 mm and 4 mm. The wings can extend a length away from the legs a distance between about 0.1 mm and about 1 mm while the slot can vary in width between about 0.1 and 2 mm. It is to be understood that these dimensions are exemplary and will vary with the need of the patient. The sides may be parallel or tapered.

As shown in FIG. 8, the legs 30 and 32 of the post 35 can have wings 36 which fit into slots of implant 38 and can have wings 40 which fit into appropriately sized slots of a core or crown 42. The post 35 can be provided with holes 37 into which a tool can be inserted to assist in flexing legs 30 and 32 for insertion into implant 38.

Referring to FIG. 9, the post-implant system of this invention is shown with one wing 44 in post 46 and one slot 48 in implant 50. The leg 52 is sufficiently flexible so that wing 44 can be positioned into and away from slot 48 by compressing exposed area 54 or releasing area 54 from compression force.

As shown in FIG. 10, the implant 50 can be provided with a hole 60 for the purpose of allowing bone to grow into the implant 50. The post 62 is provided with wings 64 for insertion into mating slots of implant 58. The post 62 also is provided with flanges 66 to position it on implant 58 as well as provide a solid seal to the implant. extension 70 to accomodate core 72. Extension 70 is provided with wing 74 which fit into slots of core 72 after compression force on post 62 has been released from flanges 66. Thus, the post 62 can be utilized to position core 72 in proper position while eliminating the need for pressure on implant 58.

Referring to FIGS. 11-15, a system of this invention is shown which permits rotational implacement of the post of this invention into the implant of this invention. The implant 80 is provided with a core 82 and vertical pathways 84 and slots 86 which are positioned at varying vertical positions. Pathways 84 permit insertion of wings 88 therein from post 90 so that the wings 88 can be positioned into slots 86. Once so positioned, key 92 is positioned into the space and pathway 84 so that rotation of the post 90 is prevented. A cement 98 can be applied into space 96 to retain key 92 in place. Since the cement 98 is easily accessible after a core or crown (not shown) is to be removed, the key of 92 can be removed if it is desired to access the implant to treat infection after the initial implant system is in place.

Figure 16:
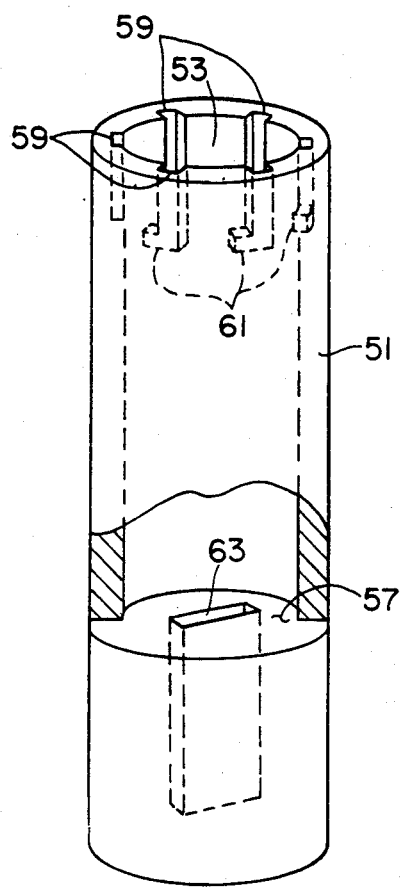
FIG. 16 is an isometric view of an implant of this invention.
Figure 17:
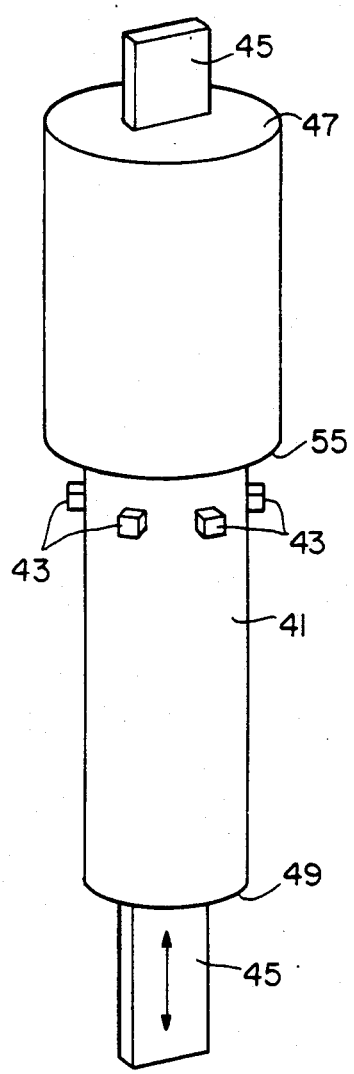
FIG. 17 is an isometric view of a post used in conjunction with the implant of FIG. 16.

Referring to FIGS. 16 and 17, an alternative implant-post-key system of this invention is shown. The post 41 includes wings 43 and a central rectangualrly shaped hole to accomodate a vertically movable key 45. The key extends beyond both ends 47 and 49 of the post 41. The implant 51 includes a central hole 53 to accomodate post 41 so that surface 49 of post 41 contacts surface 57 of implant 51. The wings 43 are inserted into vertical pathways 59 and the post 41 then is rotated so that wings 43 are inserted into slots 61. The key 45 then is inserted through post 41 into the rectangular hole 63 so as to prevent rotation of post 41.

Figures 18, 19:
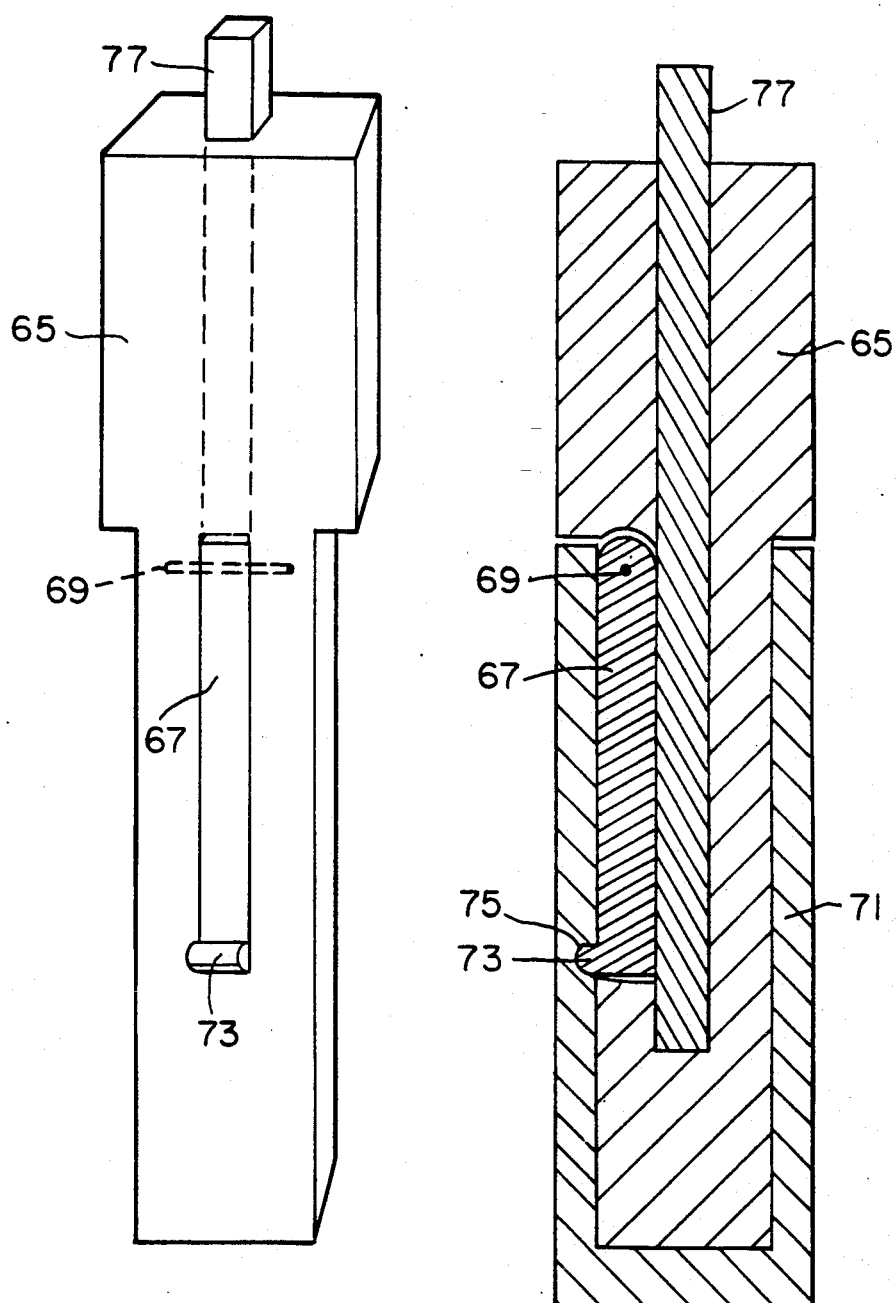
FIG. 18 is a front view of a post useful with the implant of FIG. 16.
FIG. 19 is a view of an alternative implant of this invention with the post of FIG. 18 in place.

Referring to FIGS. 18 and 19 an alternative implant-post-key system of this invention is shown. The post 65 includes a leg 67 supported by a hinge 69. The implant 71 includes a hole having a rectangular cross-section. When the post is placed into the implant 71, the leg 67 swings about hinge 69 so that lip 73 of leg 67 is positioned in slot 75 of implant 71. Thereafter key 77 is inserted into central rectangular holes in post 65 and implant 71 to prevent rotation of post 65 and to stop the leg from swinging on hinge 69.

Figure 20:
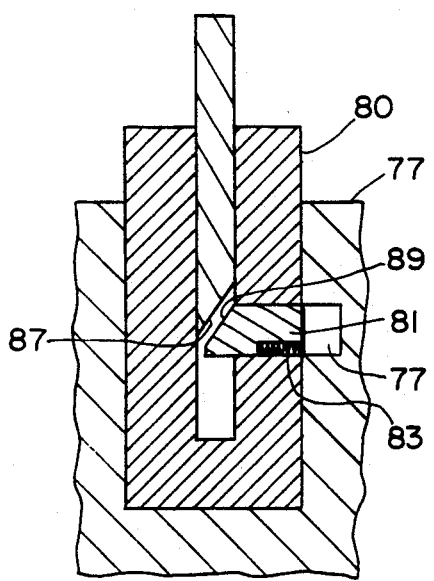
FIG. 20 illustrates an alternative post of this invention.
Figure 21:
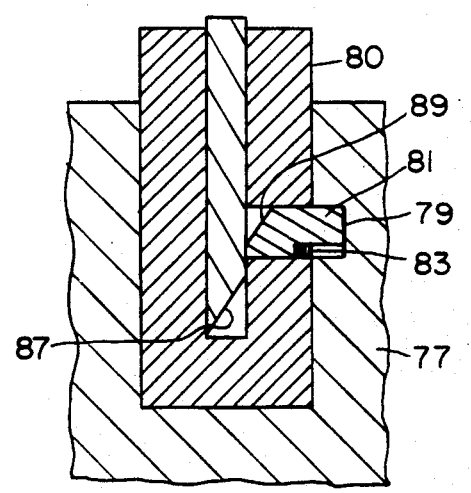
FIG. 21 illustrates the post of FIG. 20 in place in an implant.

Referring to FIGS. 20 and 21, the implant 77 includes a slot 79. The post 80 includes a spring loaded tab 81 having a spring 83 positioned as shown. When the key 85 is inserted into post 80, the inclined surfaces 87 and 89 contact each other to slide tab 81 into place in slot 79.

Referring to FIG. 22, a post 91 comprises a helical screw surface and an upper section 95. The post extends to bottom internal surface 97 by being screwed into threads 99 of the implant 100. The key 102 then is inserted into slot 104 of implant 100 to prevent rotation of the post 91.

Referring to FIGS. 23 and 24, the implant 82 includes angled internal slots 84, a central opening 86 and a key slot 88. The post 90 includes angled tabs 92 which mate with slots 84 when post 90 is rotated. After the tabs 92 are in position within slots 84, key 94 is inserted through the center of post 90 and into key slot 88 in order to retain the post 90 in place without the need for cement.

Referring to FIG. 25, the post 103 includes an upper section 105 and a lower section 107. A spring 109 is formed within the walls of sections 105 and 107. The spring 109 includes an extension or wings 111 which fits into slot 113 of implant 115. The elliptical key 117 fits through the central opening 119 of post 103 and extends into slot 121 located on the lower internal surface of implant 115 to prevent rotation of post 103.

I claim:

1. A dental system for insertion into a bore of a jaw bone of a patient which comprises:
    a dental implant adapted to fit in a bore of said jaw bone, said dental implant having a central hole extending from a top surface of said implant through a portion of the vertical height of said implant,
    at least one slot in a wall of said implant and said at least one slot open to said central hole,
    a dental post having a stem section shaped to fit into said central hole and at least one wing extending radially from said stem section and shaped to fit into one of said slots,
    and means for positioning said at least one of said wings into one of said slots, said at least one wing and said at least one slot being shaped to prevent rotation of said post in at least one direction after said positioning.

2. The dental system of claim 1 wherein means for positioning comprises a key adapted to fit within a space in said post thereby to maintain said at least one wing into said at least one slot.

3. The dental system of any one of claims 1 or 2 wherein said post has a plurality of wings and said implant has a plurality of slots.

4. The system of any one of claims 1 or 2 wherein said post has a plurality of wings at essentially the same vertical position.

5. The system of any one of claims 1 or 2 wherein said at least one wing has a shape to fit within a vertical pathway in an inner wall of said implant and said at least one wing is positioned into said slot by rotating said post.

6. The dental system of any one of claims 1 or 2 wherein said post has at least-one wing extending radially from said stem section and said implant having at least one slot in an internal wall of said implant open to said central hole.

7. A dental system for insertion into a bore of a jaw bone of a patient which comprises:
- a dental implant adapted to fit in a bore of said jaw bone, said dental implant having a central hole extending from a top surface of said implant through a portion of the vertical height of said implant and a bottom internal surface.
- at least a slot in said bottom internal surface of said implant and said slot open to said central hole,
- a dental post having a stem section shaped to fit into said central hole, said post having a second central hole extending through the vertical height of said post,
- and a key extending through said second central hole and into said slot.

8. The system of any one of claim 7 wherein said post has a plurality of wings and said implant has a plurality of slots.

9. The system of any one of claims 7 or 8 wherein said post has a plurality of wings and said implant has a plurality of slots.

10. The system of any one of claims 7 or 8 wherein at least one wing has a shape to fit within a vertical pathway in an inner wall of said implant and said at least one wing is positioned into said slot by rotating said post.

* * * * *